United States Patent [19]
Pellicciari et al.

[11] Patent Number: 5,175,320

[45] Date of Patent: * Dec. 29, 1992

[54] FLUORINATED BILE ACID DERIVATIVES, PROCESSES FOR THE PREPARATION THEREOF AND PHARMACEUTICAL COMPOSITIONS CONTAINING THEM

[75] Inventors: Roberto Pellicciari; Aldo Roda; Giuliano Frigerio, all of Milan, Italy

[73] Assignee: Giuliani S.p.A., Milan, Italy

[*] Notice: The portion of the term of this patent subsequent to Oct. 29, 2008 has been disclaimed.

[21] Appl. No.: 761,440

[22] Filed: Sep. 18, 1991

Related U.S. Application Data

[63] Continuation-in-part of Ser. No. 506,837, Apr. 9, 1990, Pat. No. 5,061,701.

[30] Foreign Application Priority Data

Apr. 17, 1989 [IT] Italy .................. 20170 A/89

[51] Int. Cl.⁵ .................................. C07J 9/00
[52] U.S. Cl. .................................... 552/554
[58] Field of Search ............................ 552/554

[56] References Cited

U.S. PATENT DOCUMENTS 5,061,701 10/1991 Pellicciari et al. .................. 514/182

Primary Examiner—Marianne M. Cintins
Assistant Examiner—Kimberly J. Kestler
Attorney, Agent, or Firm—Walter H. Schneider

[57] ABSTRACT

Compounds of general formula I

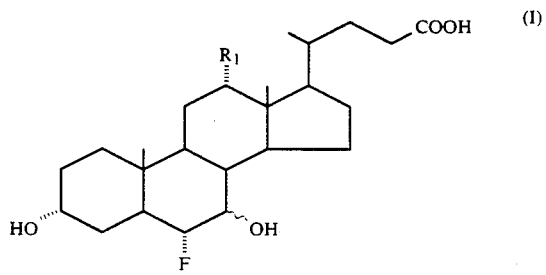

wherein $R_1$ is hydrogen or hydroxy, and the hydroxy group at the 7-position can be either in $\alpha$ or $\beta$ configuration, are valuable in human therapy. Compounds I can be prepared by fluorination of the suitably protected 6$\alpha$-hydroxy-7-keto-derivatives.

1 Claim, No Drawings

FLUORINATED BILE ACID DERIVATIVES, PROCESSES FOR THE PREPARATION THEREOF AND PHARMACEUTICAL COMPOSITIONS CONTAINING THEM

This application is a continuation-in-part of appl. Ser. No. 506,837 filed Apr. 9, 1990, now U.S. Pat No. 5,061,701.

The present invention relates to bile acid derivatives, to a process for the preparation thereof and to pharmaceutical compositions containing them.

The derivatives of the present invention have the following general formula I

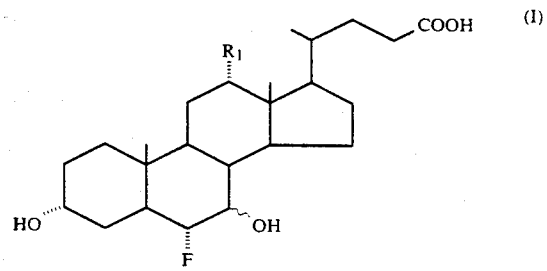

wherein $R_1$ is hydrogen or hydroxy, and the hydroxy group at 7-position can be either in $\alpha$ or $\beta$ configuration.

Therefore, compounds I are the 6-$\alpha$-fluoro derivatives of the following natural bile acids: ursodeoxycholic (UDCA) (3$\alpha$, 7$\alpha$OH), ursocholic (3$\alpha$, 7$\beta$ OH; $R_1$=OH), chenodeoxycholic (3$\alpha$, 7$\alpha$ OH) and cholic (3$\alpha$, 7$\alpha$OH; $R_1$=OOH) acids.

The present invention also relates to the physiologically acceptable salts of compounds I, as well as to possible glycine or taurine conjugated forms. Moreover, the invention also relates to the single isomers or diastereoisomers of compounds I and to the mixtures thereof.

The above cited bile acids have been used for a long time in human therapy for the treatment of biliary calculosis, as antidyspeptic, eupeptic, antidyslipidemic and choleretic agents, and generally in all those pathological conditions in which a stimulation of bile flow and a qualitative and/or quantitative change thereof are required.

Therapeutic characteristics of natural molecules promoted the development of a number of synthetic or semi-synthetic derivatives in the attempt to obtain improved drugs as regard pharmacokinetic, metabolic or chemico-physical aspects (lipophilia/hydrophilia ratio, stability, critical micellar concentration). See, for instance, EP-A-83106708.7, 84104598.2, 84109811.4, 85115611.7 and USA-P 4648995, 4460509, 4545938.

The above cited US patents particularly disclose 7-methyl, 7-hydroxy derivatives which, in comparison with the natural moleculae, should provide the advantage of a higher resistance to 7-dehydroxylation by intestinal bacterial flora, and accordingly a prolonged half-life as well as an increase in stability.

These and other advantages are provided by the compounds of the present invention, which compounds are characterized by the presence of a fluorine atom at the 6 position, the 7-position being substantially unchanged in comparison with the natural molecula, which is perse advantageous since 7-position has been found to be critical as regard pharmacological activity.

Fluorine at the 6-$\alpha$position makes the molecule less liable to 7-dehydroxylation.

Moreover, fluorinated derivatives show an increased pharmacological activity and favourable pharmacokinetic characteristics, in comparison with natural bile acids.

The compounds of the invention have a very low acute toxicity ($LD_{50}$ in the mouse per os > 5 g/kg), and are very useful particularly for the treatment of cholelithiasis, biliary dyskinesias, hypercholesterolemia, atherosclerosis, dispepsias and generally in all those pathological conditions for which the therapeutical usefulness of the known bile acids has been recognized.

The compounds of the invention, for the envisaged therapeutical uses, are administered in form of pharmaceutical compositions prepared according to known techniques and excipients, as described e.g. in "Remington's Pharmaceutical Sciences Handbook", Hack Pub. Co., N.Y. USA.

The preferred administration route is the oral one, and the daily doses, which will vary depending on the pathology to be treated and the patient's conditions, will in principle be comprised from 50 to 500 mg, one or more times a day.

Examples of suitable pharmaceutical compositions comprise capsules, tablets, sugar-coated pills, syrups, granulates, solutions, vials. The compounds of the invention can also be administered by local perfusion, before or after surgical operations, in form of dispersible solutions or powders.

The process for the preparation of compounds I is carried out according to the scheme reported hereinbelow, in which $R_2$ is a hydroxy protecting group, $R_1$ is hydrogen or a protected hydroxy group, $R_3$ is a carboxy protecting group and $R_1$ is as defined in formula I.

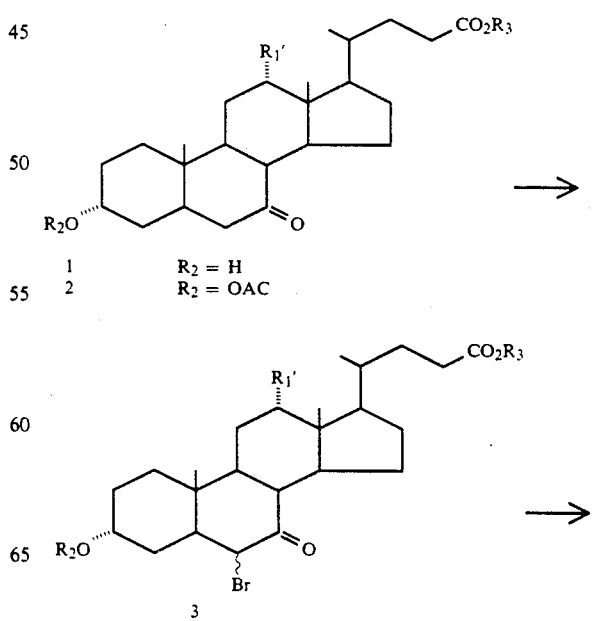

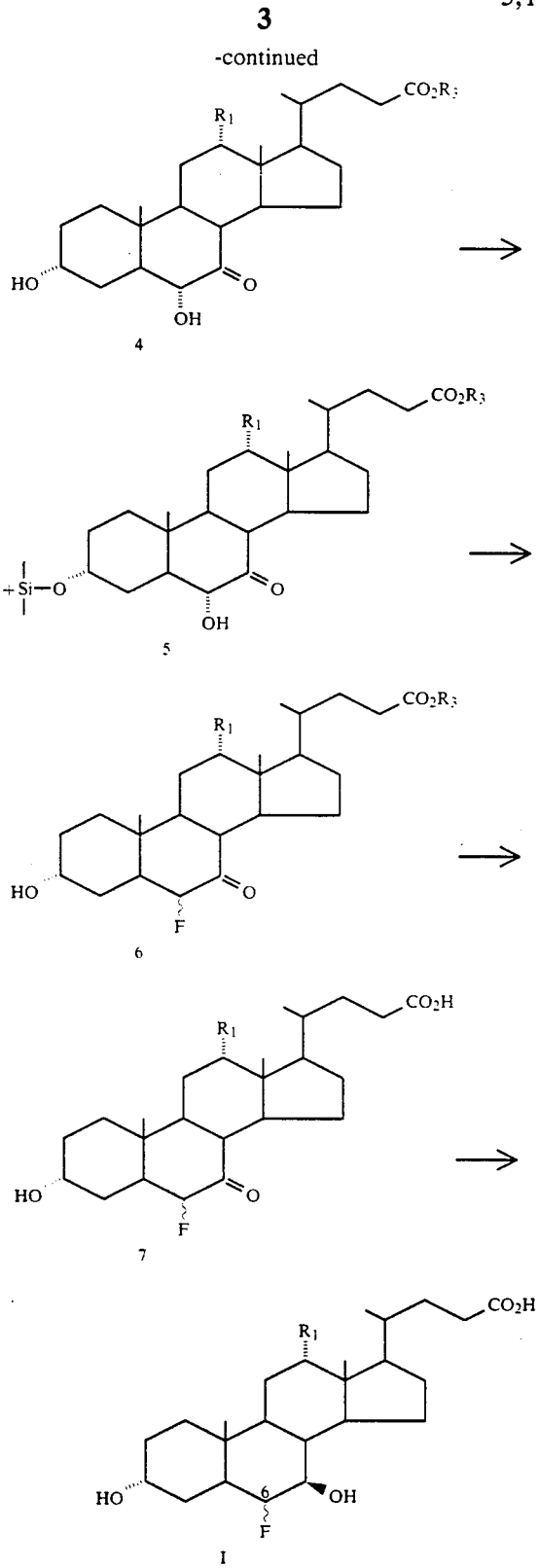

hydroxy group is sterically hindered and therefore a selective protection of the 3-hydroxy group and possibly of the 11-hydroxy group can be effected. Preferred protecting groups are, for example, silanes having bulky alkyl groups, such as tert-butyldimethyl-silyl. The hydroxy group can be replaced by the fluorine atom using an appropriate fluoride ion source, for example diethylamino-sulfur-trifluoride, (DAST) in anhydrous solvents or with quaternary ammonium fluorides, such as tetra-t-butylammonium fluoride.

Elimination of the hydroxy and carboxy protecting groups and reduction of the 7keto group give compounds of formula I.

Suitable hydroxy protecting groups are esters, such as acetates, trichloroacetates, formates, benzoates, benzyloxy carbonyl derivatives, carbonates; ethers such as tetrahydropyranyl ethers, silyl derivatives and the like. Suitable carboxy protecting groups are esters such as methyl, t-butyl, benzyl, benzhydryl, trityl, p-nitrobenzyl, trimethylsilyl and tetrahydropyranyl esters, amides, hydrazides and the like.

Although all the known protecting groups can be used as far as they are inert under the selected reaction conditions, the acetic ester is preferred as the hydroxy protecting group and the methyl ester is preferred as the carboxy protecting group.

The following examples further illustrate the invention without limiting it.

EXAMPLE 1

Preparation of 3α, 7β-dihydroxy-6α-fluoro-5β-cholanoic acid.

a) Methyl 3α, 7-keto-5β-cholanoate.

A solution of methyl 3α-hydroxy-7keto-5βcholanoate (10 g, 24.72 mmoles) in methylene chloride (40 ml) was added with acetic anhydride (3.79 g, 37.1 mmoles), triethylamine (3.63 g, 36 mmoles) and 4-pyrrolidinopyridine (0.11 g, 0.74 mmoles) and the reaction mixture was left to react for 3 hours under strong magnetic stirring, then it was diluted with methylene chloride (50 ml) and water (50 ml) and acidified with 10% hydrochloric acid. The organic phase was separated and the aqueous phase was extracted with methylene chloride (3×20 ml). The combined organic phases were washed with brine (1×30 ml), dried over sodium sulfate and concentrated under vacuum. The residue (11.0 g) was subjected to flash chromatography on silica, eluting with methylene chloride/methanol 99:1, to obtain 10.5 g. of a pure product (95%).

b) Methyl 3α-acetoxy-6-bromo-7-keto-5β-cholanoate.

A solution of methyl 3α-acetoxy-7-keto-5β-cholanoate. (5.6 g, 12.54 mmoles) in acetic acid (100 ml) was added with a bromine solution (2.8g) in acetic acid (10 ml) and immediately after with 48% hydrobromic acid (0.74 ml). The resulting reaction mixture was left to react overnight under strong magnetic stirring, then it was poured into water (300 ml) and filtered under vacuum to obtain a solid (8,03 g) which was subjected to flash chromatography on silica, eluting with methylene chloride/methanol 99.5:0.5, to yield 6.0 g of a pure product (91%).

Methyl 3α, 6α-dihydroxy-7-keto-5β-cholanoate.

A solution of methyl 3α-acetoxy-6-bromo-7-keto-5β-cholanoate (10.9 g, 19.025 mmoles) in methanol (600 ml)

The bromination reaction can be carried out using bromine in acetic acid, N-bromosuccinimide or other conventional bromination agents.

Stereospecific substitution of the bromine atom at the 6-position is usually effected by reaction with an alkali hydroxide, preferably potassium hydroxide, in an alcoholic or water-alcoholic solution. The introduced 6- was added to a solution of potassium hydroxide (24 g) in water (100 ml), dropwise, in 1 hour. The resulting mixture was left to react for 48 hours under argon atmosphere, with magnetic stirring. The reaction mixture was diluted with water (100 ml), acidified with 10% hydrochloric acid and extracted with chloroform (3×200 ml). The combined organic phases were washed with brine (1×50 ml) and dried over sodium sulfate. After evaporation of the solvent, the residue (7.7 g) was reacted with p-toluenesulfonic acid (0.5 g) in methanol (250 ml) under magnetic stirring for one night. The reaction mixture was concentrated under vacuum, taken up into chloroform (150 ml) and washed first water (3×30 ml), then with brine (1×50 ml). The organic phase was dried over sodium sulfate and concentrated under vacuum. The residue (8.0 g) was subjected to flash chromatography on silica, eluting with chloroform/methanol 98:2, to obtain 4.5 g of a pure product (56%).

d) Methyl 3α-tert-butyldimethylsilyloxy-6-α-hidroxy-7-keto-5β-cholanoate.

A solution of methyl 3α, 6α-dihydroxy-7-keto-5β-cholanoate (4.4 g, 10.45 mmoles) in anhydrous dimethylformamide (120 ml) were added with imidazole (7.4 g, 108.8 mmoles), anhydrous pyridine (1.07 ml) and tert-butyldimethylchlorosilane (3.3 g, 21.9 mmoles); the mixture was left to react for 4 hours under strong magnetic stirring, under argon atmosphere, then it was diluted with methylene chloride (100 ml), washed with water (3×50 ml), then with brine (1×50 ml). The organic phase was dried over sodium sulfate and concentrated under vacuum. The residue (6.20 g) was subjected to flash chromatography on silica, eluting with chloroform, to obtain 3.36 g of a pure product (60%).

e) Methyl 3α-hydroxy-6α-fluoro-7-keto-5β-cholanoate.

A solution of methyl 3α-tert-butyldimethylsilyloxy-6α-hydroxy-7-keto-5β-cholanoate (2.4 g, 4.49 mmoles) in methylene chloride (50 ml) was added dropwise in one hour to a solution of diethylamino-sulfur-trifluoride (2.72 ml, 20.0 mmoles) in methylene chloride (50 ml) and the mixture was left to react overnight under argon atmosphere, with magnetic stirring. The reaction mixture was washed with water (1×30 ml), subsequently with a sodium bicarbonate saturated solution (2×20 ml), finally with brine (1×30 ml). The organic phase was dried over sodium sulfate and concentrated under vacuum. The residue (2.0 g) was subjected to flash chromatography on silica, eluting with methylene chloride, to obtain 0.6 g of a pure product (32%).

f) 3α-hydroxy-6α-fluoro-7-keto-5β-cholanoic acid.

A solution of methyl 3α-hydroxy-6α-fluoro-7-keto-5β-cholanoate (0.6 g, 1.42 mmoles) in methanol (46 ml) was added to a methanol solution of 10% potassium hydroxide (82 ml) and the resulting solution was kept under magnetic stirring overnight. Then methanol was removed under vacuum, the residue was taken up into water (50 ml), acidified with 10% hydrochloric acid and extracted with methylene chloride (3×30 ml). The combined organic phases were washed with brine (1×20 ml) and dried over sodium sulfate. After evaporation of the solvent, the residue (0.62 g) was subjected to flash chromatography on silica, eluting with methylene chloride/methanol 95:5, to obtain 0.55 g of a pure product (95%).

g) 3α,7β-dihydroxy-6α-fluoro-5β-cholanoic acid.

A solution of 3α-hydroxy-6α-fluoro-7-keto-5β-cholanoic acid (0.42 g, 1.02 mmoles) in tetrahydrofuran (44 ml) was added with sodium borohydride (0.165 g, 4.36 mmoles) in methanol (11 ml) and the resulting mixture was left to react for one hour under magnetic stirring. Then the reaction mixture was diluted with ethyl acetate (20 ml), added with water (20 ml) and acidified with 10% hydrochloric acid (10 ml). The organic phase was separated, the aqueous phase was extracted with methylene chloride (3×20 ml); the combined organic phases were washed with brine (1×30 ml) and dried over sodium sulfate. After evaporating the solvent, the residue (0.42 g) was subjected to flash chromatography on silica, eluting with methylene chloride/methanol 98:2, to obtain 0.03 g of the starting product and 0.16 g of the title product (41%), the structure of which was confirmed by $^1$H-NMR, $^{13}$C-NMR, $^{19}$F-NMR and mass spectroscopies. mp 198-201° C.; IR (CHCl$_3$) 1725 (C=O); $^1$H-NMR (200 MHz, CDCl$_3$+CD$_3$OD) 0.7 (s, 3H, 18-CH ), 0.9-0.95 (m, 6H, 19-CH$_3$, 21-CH$_3$), 3.38 (m, 1H, 6-H), 3.7 (m, 2H, 3H, 7-H); $^{13}$C-NMR (200 MHz, CDCl$_3$+CD$_3$OD) 75.43 C$_3$, 79.199 C$_7$, 95.45 C$_6$, 176.24 (—COOH); $^{19}$F-NMR(CDCl$_3$+CD$_3$OD) inner standard C$_6$F$_6$, $\phi$ −5.4; m/z 391 (9.18%), 390 (34.28%), 354.4 (2.64%). C$_{24}$H$_{39}$FO$_4$.

EXAMPLE 2

3α,7α-Dihydroxy-6-fluoro-5α-cholan-24-oic acid (6-FCDCA)

The title compound was prepared according to the scheme reported on page 11, by reacting methyl 7-keto-lithocholate (1) with lithium diisopropylamide in THF at −78° C. and then with trimethyl chlorosilane in triethyl amine, the trimethylsilyl enol ether (2) was obtained. The crude silyl enol ether was then submitted to fluorination by N-fluoropyridinium triflate in refluxing acetonitrile-dichloromethane (1:3), producing the methyl 6-fluoro-7-keto lithocholate (3) with 57% yield from (1). Reduction with sodium borohydride afforded the 3α-7α-dihydroxy-6-fluoro-derivative (4) as a mixture of the two epimers with 96% yield and, finally, the alkaline hydrolysis of (4) gave the 3α. 7α-dihydroxy-6-fluoro-5β-cholan-24-oic acid (5, mp 102-5° C.) with 74% yield.

The overall yield from (1) was 40.5%.

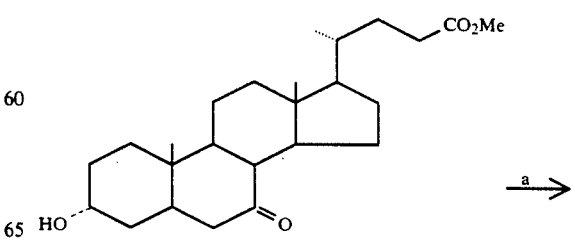

1

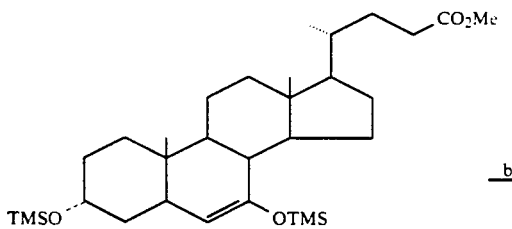

2

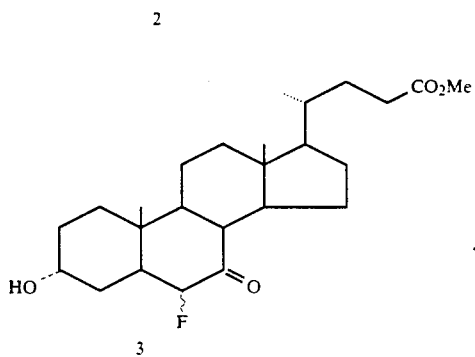

3

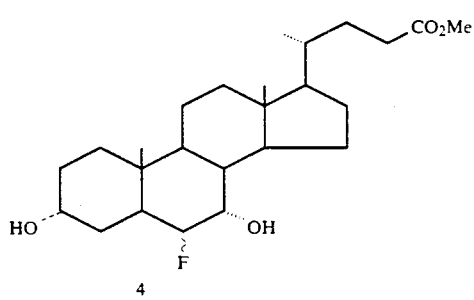

4

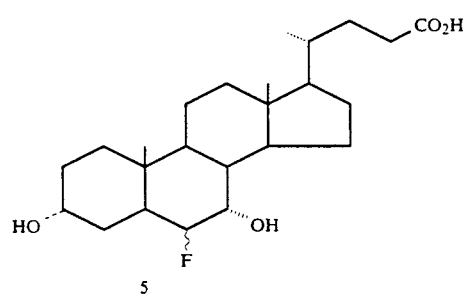

5 a LDA, TMSCl, Et₃N, THF, −78° C.;
b N-fluoropyridinium triflate, CH₃CN/CH₂Cl₂;
c NaBH₄, MeOH/THF;
d 10% KOH, MeOH

Physico chemical properties

6-FCDCA has been submitted to a series of physico-chemical determinations following a previously described protocol.

Particularly, the lypophilicity, detergency, water solubility and pKa were measured.

Data were compared with the physiological analogues CDCA and UDCA. Results are reported on Table 1.

TABLE 1

| | physico-chemical properties | | | |
|---|---|---|---|---|
| | S μmol/l | CMC mmol/l | rK' C-18 | pKa |
| UDCA | 19 | 19 | 0.4 | 5 |
| CDCA | 30 | 9 | 0.89 | 5 |
| 6-FCDCA | 80 | 10 | 0.6 | 5 | rK' = relative values

Water solubility of the protonated forms

Data on water solubility are reported on the enclosed table 1.

The water solubility of 6-FCDCA is slightly higher than that of CDCA, 80 μmol vs 30 μmol.

The detergency as evaluated by measuring the critical micellar concentration is similar to that of CDCA, with a value of 10 mmol/liter.

The lypophilicity of 6-FCDCA as evaluated by C/18 reverse phase HPLC is lower when compared with CDCA.

The value is intermediate between CDCA and UDCA.

pKa values i.e. the acidity is similar to natural analogues with a value of 5.

The preliminar physico-chemical data suggested that the introduction of a fluorine group on position 6 slightly affects the behaviour of the molecule in water in report to CDCA.

The fluorine group increases the hydrophilicity of the molecule without increasing the detergency.

This result could be a positive effect and particulary promising for increasing the hydrophilicity of a given bile acid and this effect is quite similar to that of an hydroxy group.

Biological properties

The introduction of a fluorine group in 6-position efficaciously protects the hydroxy group in 7-position to oxidation and 7-dehydroxylation as evaluated by incubation of the molecule with human stools in anaerobic conditions.

In conclusion the 6-FCDCA is a molecule less lypohilic than CDCA and more stable to intestinal bacteria.

These properties are favourable for a reduced toxicity both by a direct effect due to lypophilicity and by the prevention of toxic metabolite like lithocolic acid which can be formed in the intestine.

We claim:

1. 3α, 7αDihydroxy-6-fluoro-5β-cholan-24-oic acid of formula:

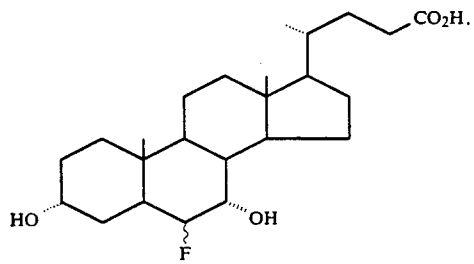

* * * * *